United States Patent
Umeda et al.

(10) Patent No.: US 9,326,752 B2
(45) Date of Patent: May 3, 2016

(54) MEASUREMENT FREQUENCY VARIABLE ULTRASONIC IMAGING DEVICE

(71) Applicant: Hitachi Power Solutions Co., Ltd., Hitachi-shi, Ibaraki (JP)

(72) Inventors: Masamichi Umeda, Hitachinaka (JP); Kaoru Kitami, Hitachinaka (JP); Natsuki Sugaya, Katsushika (JP); Masafumi Takada, Matsudo (JP)

(73) Assignee: Hitachi Power Solutions Co., Ltd., Hitachi-shi (JP)

( * ) Notice: Subject to any disclaimer, the term of this patent is extended or adjusted under 35 U.S.C. 154(b) by 271 days.

(21) Appl. No.: 13/945,548

(22) Filed: Jul. 18, 2013

(65) Prior Publication Data

US 2014/0024941 A1    Jan. 23, 2014

(30) Foreign Application Priority Data

Jul. 19, 2012  (JP) ................................. 2012-160709

(51) Int. Cl.
*A61B 8/00* (2006.01)
*A61B 8/14* (2006.01)

(52) U.S. Cl.
CPC ................. *A61B 8/14* (2013.01); *A61B 8/4209* (2013.01); *A61B 8/4461* (2013.01); *A61B 8/54* (2013.01); *A61B 8/585* (2013.01)

(58) Field of Classification Search
CPC .... A61B 8/0833; A61B 8/0841; A61B 8/483; A61B 2019/528
See application file for complete search history.

(56) References Cited

U.S. PATENT DOCUMENTS

| 6,176,840 | B1 | 1/2001 | Nishimura et al. |
| 8,038,621 | B2 * | 10/2011 | Baba et al. ................... 600/459 |
| 8,068,897 | B1 * | 11/2011 | Gazdzinski ................... 600/476 |
| 2007/0197914 | A1 | 8/2007 | Kosaku |
| 2008/0194958 | A1 | 8/2008 | Lee et al. |
| 2009/0131796 | A1 | 5/2009 | Shen |

FOREIGN PATENT DOCUMENTS

| CN | 1214267 A | 4/1999 |
| CN | 101011264 A | 8/2007 |
| JP | 58-156853 A | 9/1983 |
| JP | 5-34322 A | 2/1993 |

(Continued)

OTHER PUBLICATIONS

Korean Office Action dated Sep. 18, 2014 (five pages).

(Continued)

*Primary Examiner* — Joel Lamprecht
(74) *Attorney, Agent, or Firm* — Crowell & Moring LLP

(57) ABSTRACT

An ultrasonic imaging device includes an ultrasonic probe including a piezoelectric device transmitting ultrasonic waves to a sample and receiving echo waves, an X axis scanner and a Y axis scanner scanning the sample and positions the probe at a scanning position, a frequency controller controlling a frequency of a received signal in accordance with the position of the scanning position, a signal processing unit processing the received signal, and an image generator generating an ultrasonic wave image at the frequency based on an output of the signal processing unit. The frequency controller generates and supplies a burst signal having a predetermined frequency by a burst wave oscillator to the piezoelectric device of the ultrasonic probe to generate the ultrasonic waves having a predetermined frequency.

10 Claims, 12 Drawing Sheets

(56) References Cited

FOREIGN PATENT DOCUMENTS

| | | |
|---|---|---|
| JP | 5-232092 A | 9/1993 |
| JP | 8-320311 A | 12/1996 |
| JP | 11-114000 A | 4/1999 |
| JP | 11-304769 A | 11/1999 |
| JP | 2003-107058 A | 4/2003 |
| JP | 2003-107059 A | 4/2003 |
| JP | 2004-150875 A | 5/2004 |
| JP | 2005-58321 A | 3/2005 |
| JP | 2009-504232 A | 2/2009 |
| JP | 2012-68209 A | 4/2012 |
| TW | 370458 | 9/1999 |
| TW | 200922528 A | 6/2009 |
| TW | 201002303 A | 1/2010 |
| TW | 201211530 A1 | 3/2012 |

OTHER PUBLICATIONS

Japanese Office Action dated May 12, 2015 with partial English language translation (six (6) pages).
Taiwanese Office Action dated Apr. 28, 2015 (six (6) pages).
Japanese Office Action issued in counterpart Japanese Application No. 2012-160709 dated Aug. 25, 2015 (three (3) pages).
Chinese Office Action dated May 19, 2015 (eight pages).

* cited by examiner

MEASUREMENT FREQUENCY VARIABLE ULTRASONIC IMAGING DEVICE

CROSS REFERENCE TO RELATED APPLICATION

This application claims the foreign priority benefit under Title 35, United States Code, §119(a)-(d) of Japanese Patent Application No. 2012-160709, filed on Jul. 19, 2012 in the Japan Patent Office, the disclosure of which is herein incorporated by reference in its entirety.

BACKGROUND OF THE INVENTION

1. Field of the Invention

The present invention relates to an ultrasonic imaging device for visualizing an inside of a sample by an ultrasonic testing.

2. Description of the Related Art

Conventionally, a method of two-dimensionally, mechanically scanning with a single focus type ultrasonic probe has been used to check whether a defective (delamination and boyd) on a semiconductor or an integrated circuit is present or absent through ultrasonic waves. This testing method performs transmitting and receiving of ultrasonic waves with a single focus type ultrasonic probe with a focus on a testing object part in a structure which is a testing sample, and a gate processing of echo waves (ultrasonic waves) reflected by the testing object part to obtain intensity information and time information of the echo waves (ultrasonic waves) reflected by the testing object part.

The obtained information of the echo waves is mapped on a two-dimensional space to generate inspection image information, so that the presence or the absence of defective can be checked on the basis of the inspection image information.

JP 05-232092 A discloses as an object of the invention "to easily and accurately detect a defective in a sample" and as structure of the invention "a transducer 1 for transmitting a pulse into a sample M and receiving echoes is connected to a transceiver 2 for generating the pulse and amplifying the echoes and at a rear stage thereof a gate circuit 3 for retrieving an echo at a given interval from the echoes.

Further, the gate circuit 3 is connected to a positive comparator 4, a negative comparator 5, a positive peak holder 6, and a negative peak holder 7, and their outputs are inputted into a control unit 9".

Still further, JP 05-232092 A discloses "in the positive comparator 4 and the negative comparator 5, an earlier timing when one of the echoes first exceed a predetermined reference value is input into a delay circuit 8 which closes the gate circuit 3 after an approximately one cycle".

Recently, an ultrasonic testing method using an array type ultrasonic probe has been used also. The array type ultrasonic probe is a prove having a plurality of piezoelectric devices arranged in line. Transmission and reception of the ultrasonic waves with delay in driving the elements is made for the piezoelectric devices in accordance with the predetermined scanning positions can focus ultrasonic waves, transmitted to the testing object, on the testing object. This focuses the ultrasonic waves on a point for transmission and reception similarly to the array type ultrasonic probe by disposing a lens in normal line directions of the respective piezoelectric devices or an array of the piezoelectric devices is disposed on a curved surface.

JP 11-304769 A discloses as a problem of the invention "to provide an ultrasound test method capable of detecting defectives occurring at positions having different depths in the sample accurately through one time inspection, and as solving means of the invention" an ultrasonic prove 1 provided with an array vibrators 3 comprising a plurality of vibrating elements 3a are arranged on an acoustic lens 2 is arranged to face the sample body 10. A focus FA of the acoustic lens FA and a focus FB made by electrically converging the piezoelectric vibrator are set to have different depths to accord the focuses on respective testing planes in the sample. When it is determined that there is a defective, two focuses are equalized to a testing plane on which existence of the defective is determined for the defective testing again.

Because the array type ultrasonic probe can electronically scan a plurality of piezoelectric devices, so that the ultrasound test can be performed more rapidly than the mechanical scanning by the single focus type ultrasonic probe.

JP 2003-107059A discloses as a problem of the invention "to provide an ultrasonic imaging device and a measuring method thereof which are simplified in an oscillator structure and capable of using a burst wave signal, if necessary, in a range where no interference occurs by smoothly varying transmission waves from a pulse signal to a burst wave signal". Further, JP 2003-107059A discloses as solving means of the invention "It is an ultrasonic imaging device driving a ultrasonic probe 14 with a transmission wave signal to generate ultrasonic waves 16 and irradiating a sample 18 with the ultrasonic waves, detecting and converting reflected waves returning from the sample with the ultrasonic prove into a received wave signal, displaying on a display device an image of a given testing part of the sample through image display processing on the basis of the received wave signal. Only a burst wave oscillator 12 is provided to output a burst wave signal as a means for outputting the transmission wave signal and the minimum number of waves of the burst wave signal outputted by the burst wave oscillator is equal to or smaller than 1. The number of the waves of the signal outputted by the burst wave oscillator is controlled by a controller 15.

JP 2003-107059A discloses at a paragraph 0017 as an object of the invention "to provides the ultrasonic imaging device capable of measurement at a high resolution and image generation by narrowing a frequency band to decrease attenuation affection in order that the burst wave signal can be used, if necessary, in the range where no interference occurs by smoothly varying the transmission waves from the pulse signal to the burst wave signal with a structure of a circuit part of the oscillator generating the transmission waves simplified".

However, JP 2003-107059A does not disclose on selection of an optimal frequency for a measuring sample.

A frequency optimal for visualizing an inside of the sample depends on a material forming the sample. Accordingly, it should be done to set an optimal ultrasonic wave frequency depending on the material also in a case where any one is used between the single focus ultrasonic probe or an array type ultrasonic probe.

However, conventionally, a frequency of the measurable ultrasonic waves was fixed for each ultrasonic sensor (ultrasonic probe). Accordingly, to change the frequency of the ultrasonic waves, not few ultrasonic wave sensors (ultrasonic probes) should have to be changed. Further, in the conventional ultrasonic sensor (ultrasonic probes), it have not be able to perform measurements with frequency of the ultrasonic waves being successively changed and compare the ultrasonic wave image in quality.

SUMMARY OF THE INVENTION

An aspect of the present invention provides an ultrasonic imaging device capable of selecting an optimal frequency for visualizing an inner structure of the sample with the ultrasonic waves.

An aspect of the present invention provides a measurement frequency variable ultrasonic imaging device comprising:

an ultrasonic probe including a piezoelectric device transmitting ultrasonic waves to a sample and receiving an ultrasonic waves reflected, scattered, and refracted by the sample to output a received signal;

a scanner scanning the sample with the ultrasonic probe and positioning the ultrasonic probe at a [predetermined] scanning position;

a frequency controller controlling a frequency of the received signal in accordance with the scanning position;

a signal processing unit processing the received signal; and an image generator generating an ultrasonic wave image at the predetermined frequency on the basis of an output signal of the signal processing unit.

Other means will be described in the embodiments for carrying the invention.

According to the invention, an ultrasonic imaging device can be provided which can select a frequency optimal for visualizing the inner structure of the sample.

BRIEF DESCRIPTION OF THE DRAWINGS

The object and features of the present invention will become more readily apparent from the following detailed description taken in conjunction with the accompanying drawings in which.

DETAILED DESCRIPTION OF THE INVENTION

Hereinafter with reference to drawings will be described in detail embodiments for carrying out the invention.
(Structure of First Embodiment)

Figure 1:
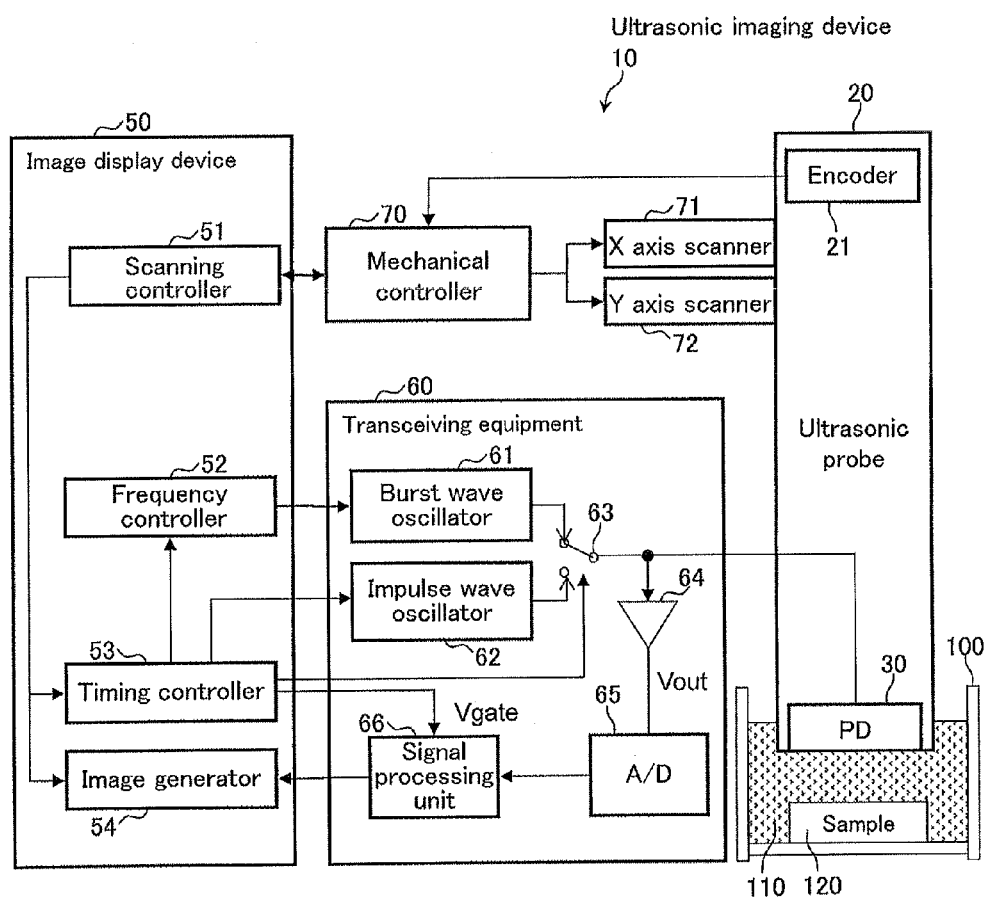
FIG. 1 is a block diagram of an ultrasonic imaging device according to a first embodiment.

FIG. 1 is a block diagram of an ultrasonic imaging device according to a first embodiment.

An ultrasonic imaging device 10 (measuring frequency variable ultrasonic imaging device) controls a frequency of echo waves, i.e., the received waves by controlling a frequency of transmission ultrasonic waves. In the first embodiment, a transceiving equipment 60 is provided with a burst wave oscillator 61 and a switch 63 and outputs and applies the burst signal to a piezoelectric device 30 to change a frequency fx of the ultrasonic waves transmitted by the piezoelectric devices 30.

The ultrasonic imaging device 10 includes an ultrasonic probe 20 for performing transmission and reception of the ultrasonic waves, an image display device 50 for displaying an ultrasonic wave image by integrally controlling the ultrasonic imaging device 10, the transceiving equipment 60 for outputting and inputting electric signals with the ultrasonic probe 20, an X axis scanner 71, a Y axis scanner 72, and a mechanical controller 70 for controlling the X axis scanner 71 and the Y axis scanner 72. The ultrasonic probe 20 is supported by the X axis scanner 71 and the Y axis scanner 72 and immerged in water 110 with which a water tank 100 is filled to allow the piezoelectric device (PD) 30 to face a sample 120.

The ultrasonic probe 20 includes an encoder 21 for detecting a scanning position of the ultrasonic probe 20 and the piezoelectric device 30 for converting the electric signal into the ultrasonic wave signal vice versa. The piezoelectric device 30 is a single focus type ultrasonic probe.

The image display device 50 includes a scanning controller 51 for controlling the scanning position of the ultrasonic probe 20, a frequency controller 52 for controlling a frequency of the ultrasonic waves; the frequency controller 52 for controlling a frequency of the ultrasonic waves; a timing controller 53 for controlling transmission and reception timing of the ultrasonic waves, and an image generator 54 for generating an ultrasonographic image. The transceiving equipment 60 includes the burst wave oscillator 61 for generating an electric signal of burst waves, an impulse wave oscillator 62 for generating an electric signal of the impulse, the switch 63, an amplifier 64 for amplifying the received signal received by the ultrasonic probe 20, an A/D converter 65 for converting the received signal of an analog signal to a digital signal, and a signal processing unit 66 for processing the received signal.

The scanning controller 51 is connected to the mechanical controller 70 (scanner) for inputting from and outputting toward the mechanical controller 70. The scanning controller 51 controls a scanning position of the ultrasonic probe 20 with the mechanical controller 70, the X axis scanner 71, and the Y axis scanner 72 (scanner) and receives a current scanning position information of the ultrasonic probe 20 from the mechanical controller 70.

An output side of the mechanical controller 70 is also connected to the X axis scanner 71 and the Y axis scanner 72. An output of the encoder 21 of the ultrasonic probe 20 is connected to the mechanical controller 70. The mechanical controller 70 detects the scanning position of the ultrasonic probe 20 from an output signal of the encoder 21 and controls the X axis scanner 71 and the Y axis scanner 72 to locate the ultrasonic probe 20 at the instructed scanning position. The mechanical controller 70 receives a control instruction for the ultrasonic probe 20 from the scanning controller 51 and in response to this transmits scanning position information to the ultrasonic probe 20.

The timing controller 53 transmits a transmission and reception timing signal (information) to the transceiving equipment 60 on the basis of the scanning position information of the ultrasonic probe 20 obtained from the scanning controller 51 and frequency information of the ultrasonic wave to the frequency controller 52.

The frequency controller 52 instructs the burst wave oscillator 61 to output only predetermined number of pulses of the burst waves of a predetermined frequency on the basis of the frequency information of the ultrasonic wave outputted by the timing controller 53.

The burst wave oscillator 61 outputs a predetermined number of pulses of the burst waves with a predetermined frequency to the piezoelectric device 30 on the basis of the signal outputted by the frequency controller 52.

The impulse wave oscillator 62 generates and transmits an impulse wave to the piezoelectric device 30 on the basis of the timing signal outputted by the timing controller 53.

The switch 63 performs switching to output either of the burst waves or the impulse wave to be outputted to the piezoelectric device 30 on the basis of the output signal of the timing controller 53.

The piezoelectric device 30 is a device in which electrodes are attached to both sides of a piezoelectric film and comprises ZnO, ceramics, or a Fluorine system copolymer.

The piezoelectric device 30 transmits ultrasonic waves from the piezoelectric film in response to impression of a voltage between both electrodes. Further the piezoelectric device 30 converts echo waves (received waves) received by the piezoelectric device into a received signal which is a voltage generated between both the electrodes. The amplifier 64 is a device for amplifying the received signal to output an output signal Vout. The A/D converter 65 converts the amplified received signal into a digital signal from an analog signal.

The signal processing unit 66 is a unit which performs a signal processing of the received signal. The signal processing unit 66 cuts out a predetermined period of the received signal using a gate pulse Vgate outputted by the timing controller 53. The signal processing unit 66 outputs amplitude information at a predetermined period or time information of the received signal at a predetermined terminal to the image generator 54.

The image generator 54 generates an ultrasonographic image at a predetermined frequency on the basis of the output signal of the signal processing unit 66.
(Operation of the Ultrasonic Imaging Device)

A sequential operation of the ultrasonic imaging device 10 will be described with reference to FIG. 1.

The scanning controller 51 scans the ultrasonic probe 20 in a positive X direction to obtain data from pixels on one line. When detecting that the ultrasonic probe 20 is positioned at an end in the X direction, the scanning controller 51 shifts the ultrasonic probe 20 by a predetermined pitch and scans with the ultrasonic probe 20 in a negative X direction. The scanning controller 51 repeats this operation to perform scanning at a predetermined region.

The timing controller 53 of the image display device 50 receives the scanning position information of the ultrasonic probe 20 in the X and Y directions from the scanning controller 51, instructs the frequency controller 52 on the frequency based on the scanning position information in the Y direction, instruct the transceiving equipment 60 to transmit the ultrasonic waves on the basis of the scanning information in the X direction, and outputs the gate pulse Vgate for signal processing of the received signal.

The transceiving equipment 60 selects either of the burst signal outputted by the burst wave oscillator 61 or the impulse signal outputted by the impulse wave oscillator 62 with the switch 63 to transmit the selected signal to the ultrasonic probe 20. Further the transceiving equipment 60 amplifies the received signal of the echo waves (received waves) received by the ultrasonic probe 20 and then converts an output of the amplifier 64 into a digital signal with the A/D converter 65. The signal processing unit 66 processes the received signal (digital signal) on the basis of the gate pulse Vgate inputted by the timing controller 53 and transmits the processed signal to the image display device 50.

The image display device 50 visualizes an inner structure of the sample 120 with the scanning position obtained by the scanning controller 51 as a pixel position and information of the received signal processed by the transceiving equipment 60 as brightness information of the pixel for displaying. The ultrasonographic image indicating the inside of the sample 120 may be generated on the basis of any of information based on the amplitude information of the received signal or information of time while the received signal exceeds a predetermined amplitude.

Figure 2:
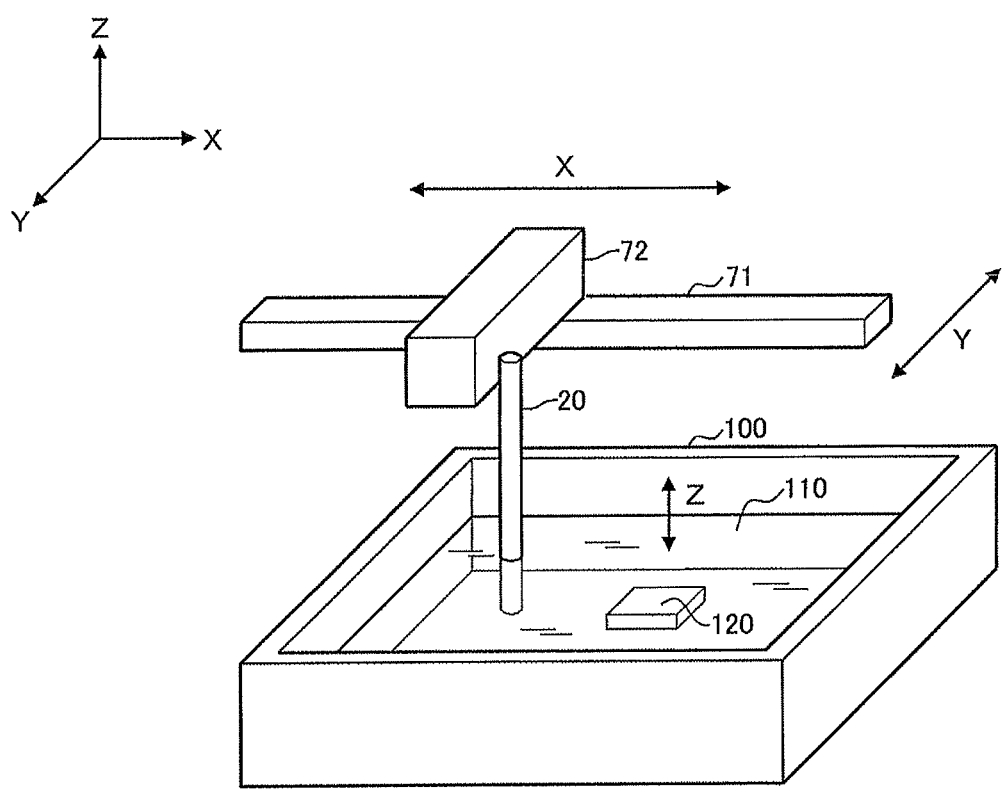
FIG. 2 is a partial perspective view of the ultrasonic imaging device according to the first embodiment to show a scanning method.

FIG. 2 is a partial perspective view of the ultrasonic imaging device according to the first embodiment to show a scanning method.

In FIG. 2, only the X axis scanner 71, the Y axis scanner 72, and the ultrasonic probe 20 are shown as a part of the ultrasonic imaging device 10.

The X axis scanner 71 is for shifting the Y axis scanner 72 in positive and negative X directions. The Y axis scanner 72 is a device for shifting the ultrasonic probe 20 in the positive and negative Y directions.

The ultrasonic probe 20 has a hollow cylindrical shape provided with the piezoelectric device 30 (see FIG. 1) at a tip thereof and the encoder 21 (see FIG. 1). The ultrasonic probe 20 is immersed into a water 110 with which the water tank 100 is filled and arranged above the sample 120 to face the sample 120 with a given distance in the Z direction.
(Operation of the First Embodiment)

Figure 3A:
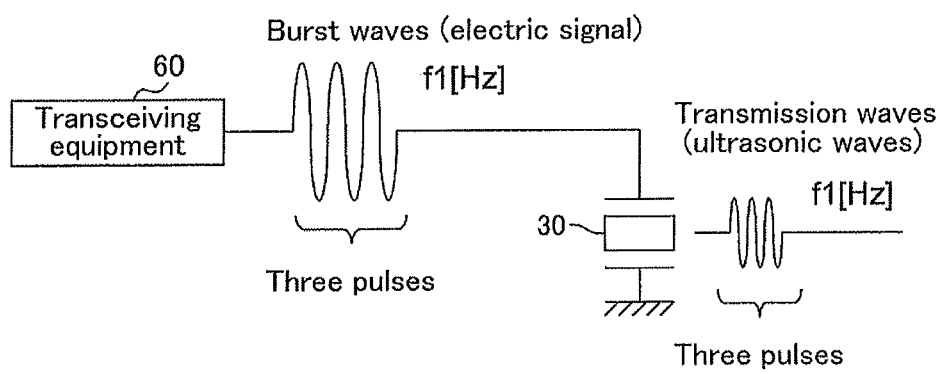
FIGS. 3A and 3B are illustrations showing a method of changing a transmission frequency according to the first embodiment.
Figure 3B:
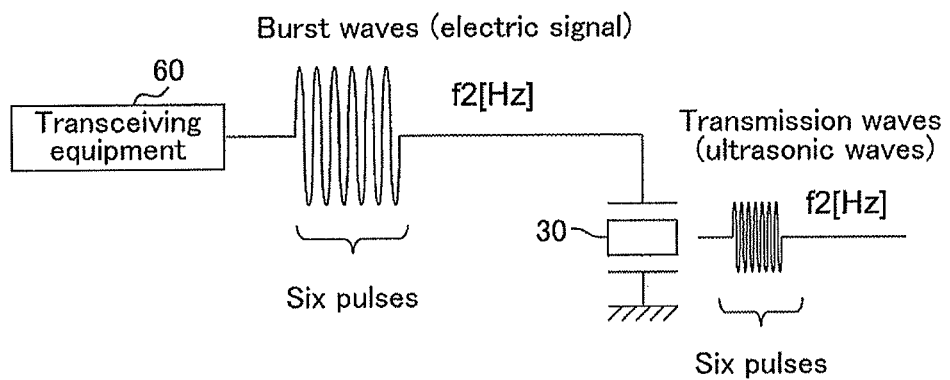

FIGS. 3A and 3B are illustrations showing a method of changing a transmission frequency according to the first embodiment.

FIG. 3A shows an example of the burst signal having a frequency f1 [Hz].

The transceiving equipment 60 outputs the burst signal (electric signal) including three pulses at a frequency f1 [Hz]. The piezoelectric device 30 outputs the ultrasonic signal including three pulses at the frequency f1 [Hz] based on the electric signal. According this the transceiving equipment 60 controls the frequency of the ultrasonic waves to control a frequency of the received signal obtained by converting the ultrasonic waves into an electric signal.

FIG. 3B shows an example of a burst signal with a frequency f2 [Hz].

The transceiving equipment 60 outputs the burst signal (electric signal) having six pulses at the frequency f2 [Hz]. The piezoelectric device 30 outputs the ultrasonic signal having six pulses at the frequency f2 [Hz] in response to the electric signal. According to this, the transceiving equipment 60 controls the frequency of the ultrasonic waves, which controls the frequency of the received signal, being an electric signal converted from the ultrasonic waves.

Figure 4A:
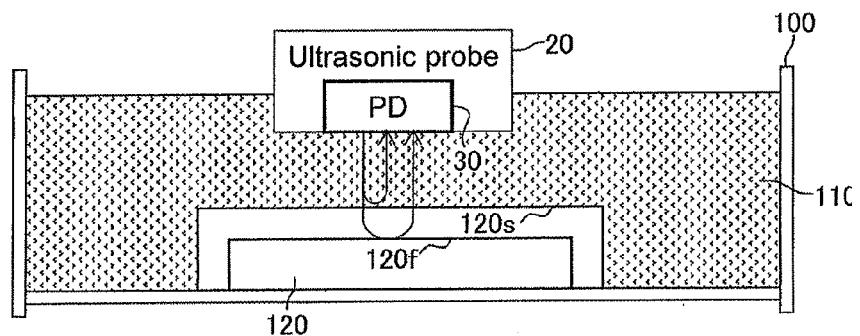
FIG. 4A is a cross section view of an ultrasonic probe and a sample.
Figure 4B:
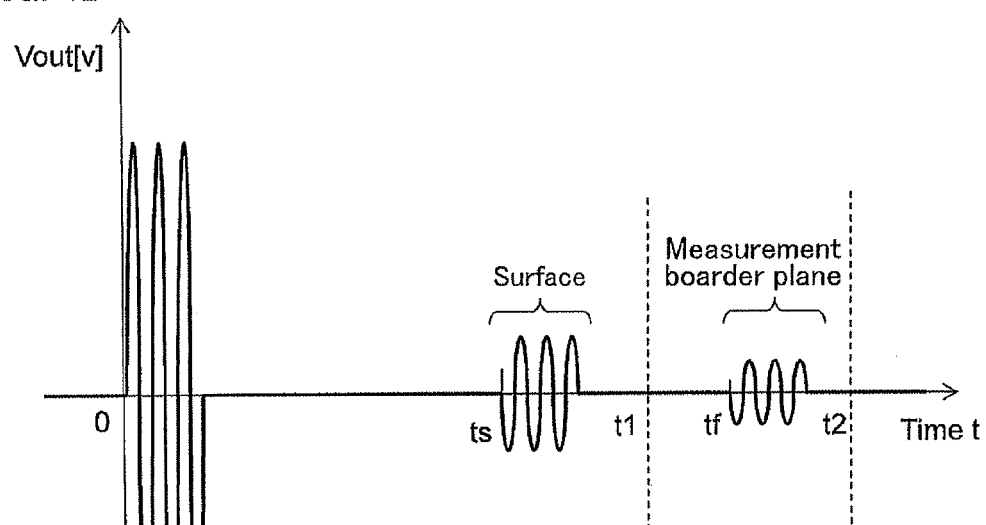
FIGS. 4B and 4C are charts showing an operation example of the ultrasonic imaging device according to the first embodiment.
Figure 4C:

FIGS. 4A to 4C show an operational example of the ultrasonic imaging device according the first embodiment.

FIG. 4A shows the ultrasonic probe 20 of the ultrasonic imaging device 10 and a sample 120.

The sample 120 has the surface 120s and a measurement border plane 120f. When the ultrasonic waves are transmitted by the ultrasonic probe 20 and reflected by the surface 120s and a measurement boarder plane 120f to generate echo waves which are received by the ultrasonic probe 20 as shown by the solid curved lines with arrows in FIG. 4A.

FIG. 4B shows a relation between the ultrasonic waves and the echo waves in an output voltage of the piezoelectric device 30. The axis of abscissa indicates time similarly to FIG. 4A. The vertical axis of FIG. 4B shows a voltage of the output signal Vout amplified by the amplifier 64.

The three pulses at time 0 are burst waves for causing the ultrasonic probe 20 to transmit the ultrasonic waves.

Three pulses at time is are the received signal corresponding to the echo waves received by the ultrasonic probe 20. The echo waves are waves reflected by the surface 120s.

Three pulses at time tf is a received signal corresponding to the echo waves received by the ultrasonic probe 20. The echo waves are waves reflected by the measurement boarder plane 120f.

FIG. 4C is a drawing indicating the gate pulse Vgate for extracting the echo waves.

The axis of the abscissa indicates a common time base. The axis of ordinate indicates a voltage of the gate pulse Vgate.

The gate pulse Vgate turns on from time t1 to t2 and off before time t1 and after time t2. Visualization of a status of the measurement boarder plane 120f can be provided by extracting the signal for ON period of the gate pulse Vgate from the output signal Vout of the piezoelectric device 30 shown in FIG. 4B to obtain an amplitude of the signal.

(Inspecting Method Using the Ultrasonographic Image)

An operation of an image display device according to the first embodiment will be described.

In performing the ultrasound test for the sample 120, the operator places the sample 120 on the bottom of the water tank 100.

The operator obtains the ultrasonographic image using the impulse signal to make the measurement boarder plane 120f clear as an inspection target of the sample 120.

The operator confirms an echo interval of the measurement boarder plane 120f with reference to the ultrasonographic image of the sample 120 using the impulse signal. There is a tendency that a resolution in the Z direction decreases when the number n of the waves is too many and frequency components of the ultrasonic wave includes frequency components other than a desired frequency components when the number of the waves n is too small. The higher the frequency fx of the burst signal becomes, the more the resolution of the image is improved by making the focus of the ultrasonic waves smaller. However, this may result in deterioration in a signal to noise ratio of the image due to attenuation in the water 110 and the inside of the sample 120.

Figure 5:
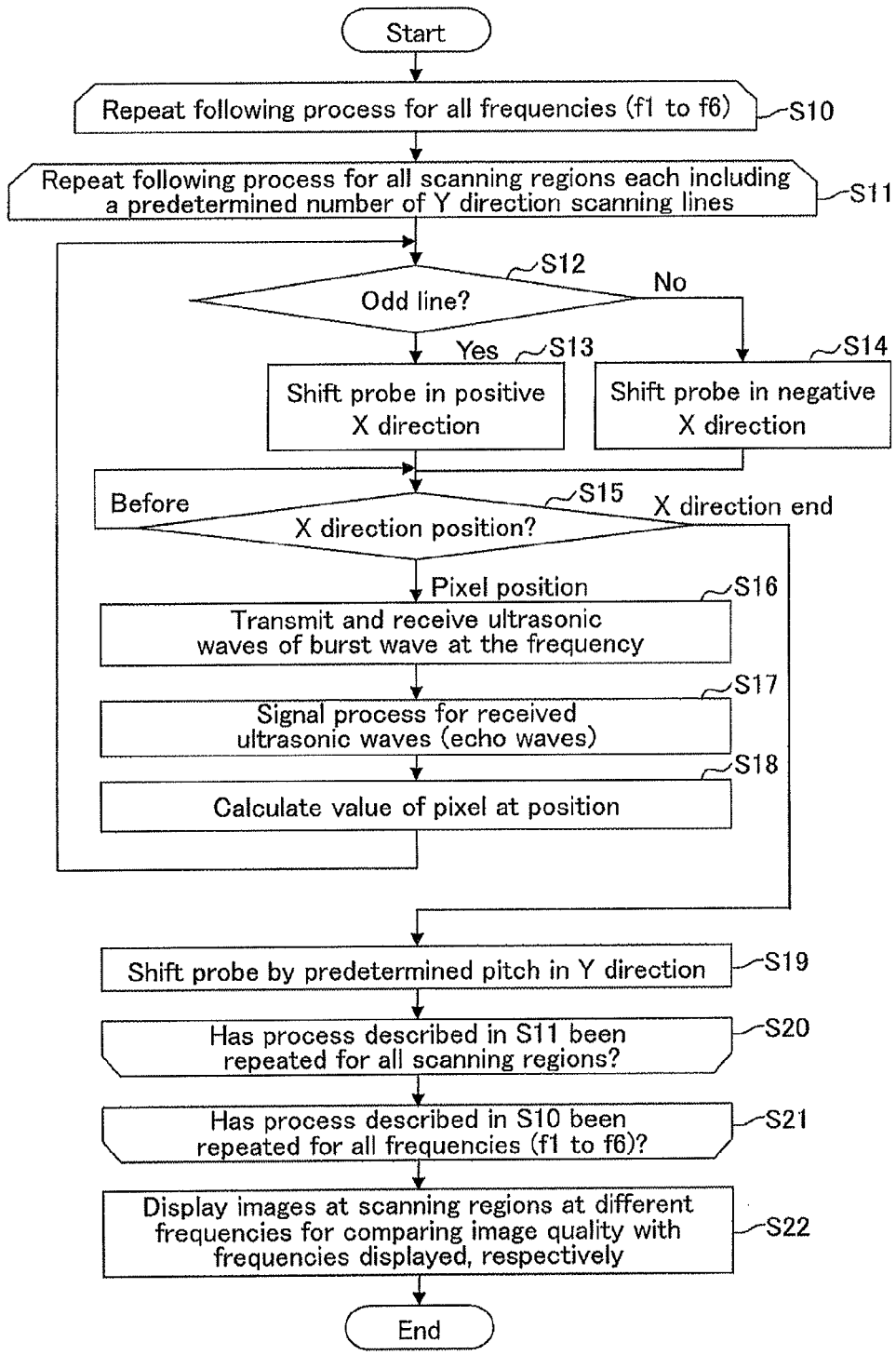
FIG. 5 is a flowchart showing a generation process of the frequency-varied image according to the first embodiment.

Further the operator switches the signal for the ultrasonic probe 20 is switched from the impulse signal to the burst signal and performs a generation process of frequency-varied images 130 shown in FIG. 5 and determines an optimal frequency fo on the basis of the frequency-varied images 130.

The operator obtains the ultrasonographic image using the burst signal of the determined optimal frequency fo as an optimal ultrasonographic image of the measurement boarder plane 120f of the sample 120 to estimate defectives inside the sample 120.

FIG. 5 is a flowchart showing a generation process of the frequency-varied image according to the first embodiment.

When a generation process for the frequency-varied images 130 is started, the image display device 50 repeats the following process including the steps S10 to S22 for all frequencies f1 to f6.

In a step S11, the scanning controller 51 of the image display device 50 repeats the following operation for the predetermined scanning region (lines) in the Y direction. The predetermined scanning region in the Y direction is the number of lines for each frequency.

In a step S12, the scanning controller 51 of the image display device 50 determines whether the current line is on an odd number line in the Y direction or not. When the determination condition is established (Yes), the scanning controller 51 performs the process in a step S13. When the determination condition is not established (No), the scanning controller 51 performs the process in a step S14.

In the step S13, the scanning controller 51 of the image display device 50 scans in the positive X direction with the ultrasonic probe 20 to perform the process in a step S15.

In the step S14, the scanning controller 51 of the image display device 50 scans in the negative X direction with the ultrasonic probe 20.

In the step S15, the scanning controller 51 of the image display device 50 determines a position in the X direction. The scanning controller 51 repeats the determination in the step S15 before the position in the X direction reaches a predetermined position. When the position in the X direction is at the predetermined pixel position, the scanning controller 51 performs the process in a step S16. When the position is at an end in the X direction, the scanning controller 51 performs a process in a step S19.

In the step S16, the timing controller 53 of the image display device 50 controls transmission and reception of the ultrasonic waves at the frequency. In other words, the timing controller 53 outputs the burst signal at the frequency through the frequency controller 52 and the burst wave oscillator 61, switches the switch 63 to an output side of the burst wave transmitter to output the burst signal to the piezoelectric device 30. According to this, the piezoelectric device 30 transmits the ultrasonic waves at the frequency and receives the echo waves (reflected waves) to convert the echo waves into the received signal. The received signal is amplified by the amplifier 64 and converted into a digital signal by the A/D converter 65. An output of an A/D converter 65 is input into the signal processing unit 66.

In a step S17, the signal processing unit 66 of the transceiving equipment 60 performs a signal processing for the received signal. The signal processing unit 66 cuts out the received signal on the basis of the gate pulse Vgate and transmits the amplitude information of the received signal or the time information when the received signal starts vibrations having a predetermined value to the image generator 54.

In a step S18, the image generator 54 of the image display device 50 calculates a value of the pixel at the position and processing returns to the process in a step S12.

In the step S19, the scanning controller 51 of the image display device 50 shifts the ultrasonic probe 20 by a predetermined pitch in the positive Y direction.

In a step S20, the scanning controller 51 of the image display device 50 determines whether the process has been repeated over the predetermined scanning range (line) in the Y direction. When the determination condition is not established, the scanning controller 51 returns to the process in a step S11.

In a step S21, the image display device 50 determines the process has been repeated for all frequencies f1 to f6. When the determination condition is not established, the image display device 50 returns to the process in a step S10.

Figure 6:
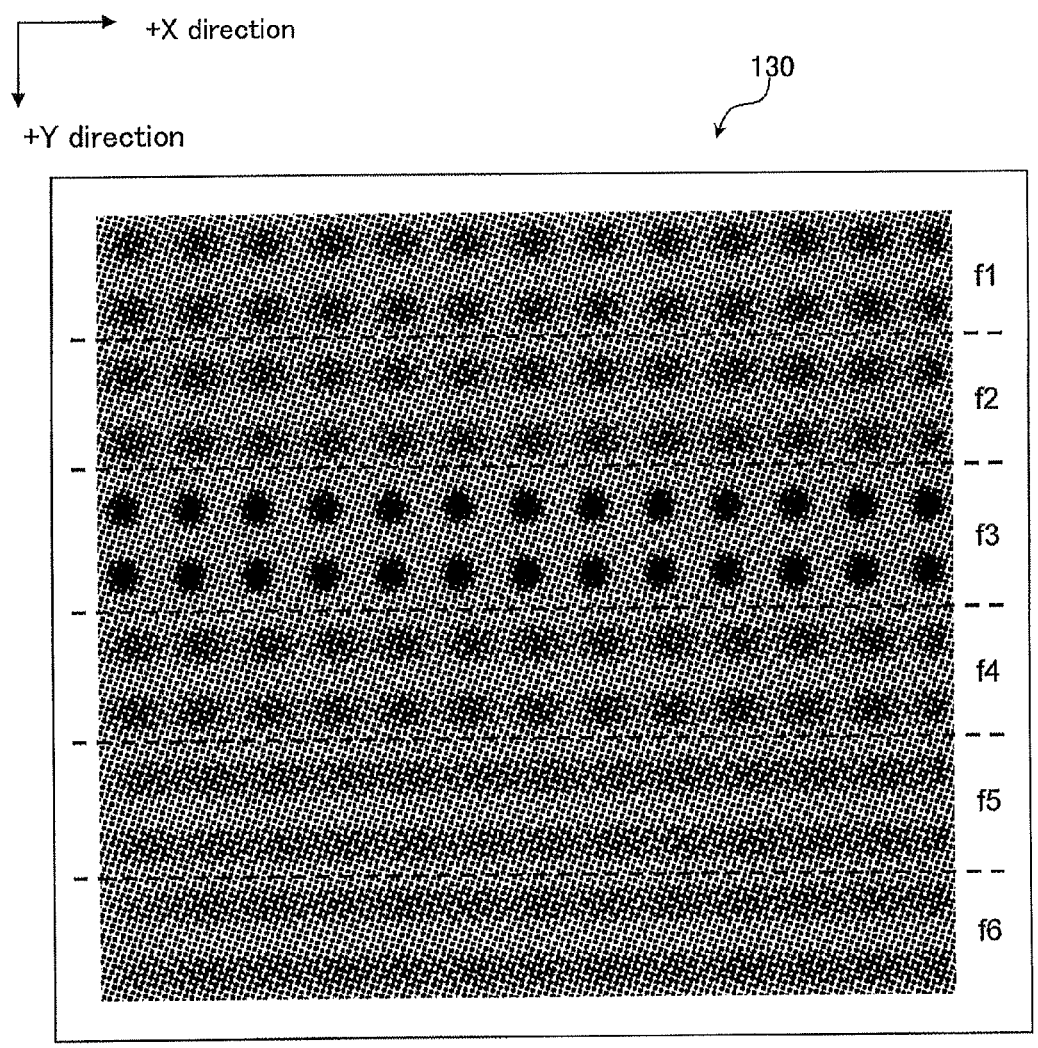
FIG. 6 is an illustration showing an example of a frequency-varied image in the first embodiment.

In a step S22, the image display device 50 displays respective frequencies of the ultrasonic waves and image lines in respective ranges in the frequency-varied images 130 to enable to compare image lines scanned at respective frequencies with the displayed frequencies as shown in FIG. 6.

FIG. 6 is a drawing showing an example of a frequency variable image in the first embodiment. A right direction in FIG. 6 indicates a positive X direction. A downward direction in FIG. 6 indicates a positive Y direction.

The ultrasonic imaging device 10 sets the frequency of the burst waves supplied to the piezoelectric device 30 to the frequency f1. Further, after shifting the ultrasonic probe 20 to the right upper part, the ultrasonic imaging device 10 performs scanning in the right direction in FIG. 6, i.e., the positive (+) X direction. When detecting the position of the ultrasonic probe 20 is at an end in the positive X direction, the ultrasonic imaging device 10 shifts the ultrasonic probe 20 in the Y direction by a predetermined pitch, and then the ultrasonic imaging device 10 performs scanning in the left direction being the negative X direction. The ultrasonic imaging device 10 repeats this predetermined numbers of times to obtain pixel values over a predetermined number of Y lines.

The ultrasonic imaging device 10 sets the frequency of the burst waves supplied to the piezoelectric device 30 to the frequency f2, obtaining pixel values over a predetermined number of Y lines, to obtain an image parts at the frequency f2. Hereinafter, the ultrasonic imaging device 10 repeats this for frequencies f3 to f6.

The frequency-varied image 130 has a region in which scanning is performed at the frequency f1, a region in which scanning is performed at the frequency f2, a region in which scanning is performed at the frequency f3, a region in which scanning is performed at the frequency f4, a region in which scanning is performed at the frequency f5, and a region in which scanning is performed at the frequency f6 in a vertical order from the upper region. The frequencies of inspection are shown on the right hand of the regions subjected to inspection at respective frequencies.

FIG. 6 shows that out of these regions a region as a result of the inspection at the frequency f3 is most preferable. In the case of FIG. 6, the frequency is set to the frequency f3 and the visualization of the sample 120 is performed again to generate a most preferable image in a short period.

(Advantageous Effect of First Embodiment)

The first embodiment described above has following advantageous effects.

(A) The ultrasonic imaging device 10 provides an image by one measurement operation with a single ultrasonic probe 20 by only one time including partial images obtained in which the frequency is varied over the image shown in FIG. 6.
(B) The ultrasonic imaging device 10 visualizes as one sheet of image with the frequency varied stepwise. Accordingly, the operator can visually determine the optimal frequency fo for inspection.
(c) The operator can easily determine the optimal frequency fo. Accordingly, the ultrasonic imaging device 10 can generate an image with a high resolution using the optimal frequency fo.

(Structure According to the Second Embodiment)

Figure 7:
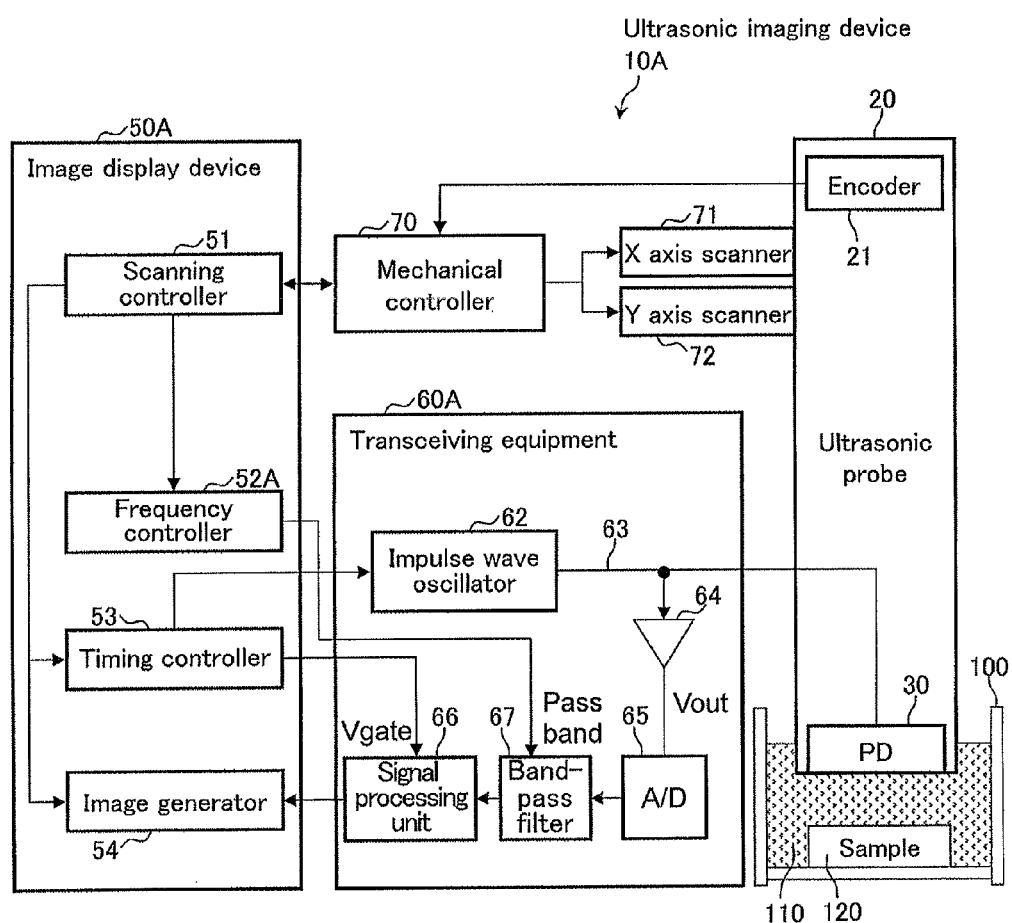
FIG. 7 is a block diagram of an ultrasonic imaging device according to a second embodiment.

FIG. 7 is a block diagram of an ultrasonic imaging device according to the second embodiment.

An ultrasonic imaging device 10A according to the second embodiment extracts a predetermined frequency component by applying the received signal to the band-pass filter 67.

The ultrasonic imaging device 10A includes an ultrasonic imaging device 50A which is different from the image display device 50 and a transceiver 60A which are different from those of the ultrasonic imaging device 10 according to the first embodiment (see FIG. 1).

The image display device 50A includes a frequency controller 52A which is a different point from the frequency controller 50 (FIG. 1). An output side of the scanning controller 51 is connected to the frequency controller 52A. An output side of the frequency controller 52A is connected to a band-pass filter 67 of a transceiver 60A which will be described later.

The frequency controller 52A controls the frequency of the received signal to a predetermined frequency according to a scanning position of the ultrasonic probe 20.

Unlike the transceiving equipment 60 according to the first embodiment, the transceiver 60A does not include the burst wave oscillator 61 and the switch 63, but the band-pass filter 67 instead. An output side of the A/D converter 65 is connected to the band-pass filter 67. The signal processing unit 66 is connected to the output side of the band-pass filter 67. The band-pass filter 67 is further connected to an output side of the frequency controller 52A. The band-pass filter 67 controls a pass band of the received signal to a predetermined band according to the scanning position of the ultrasonic probe 20.

(Operation of Second Embodiment)

With reference to FIG. 7, will be described an operation of the ultrasonic imaging device according to the second embodiment.

In performing the ultrasound test of the sample 120, the operator places the sample 120 on the bottom of the water tank 100 like the first embodiment.

The operator obtains the ultrasonographic image by the impulse signal to make the measurement boarder plane 120f clear as a target like the first embodiment. During this operation, the band-pass filter 67 is set to all signals in all frequency bands to pass therethrough.

The operator confirms an echo interval of the measurement boarder plane 120f with reference to the ultrasonographic image of the sample 120 by the impulse signal, sets timing when the gate pulse Vgate is made ON, and sets the pass band of the received signal to frequencies f1 to f6. The operator further performs generation process of the frequency-varied images 130 shown in FIG. 8 to determine an optimal frequency fo on the basis of the frequency-varied images 130.

The operator obtains the ultrasonographic image at the determined optimal frequency as an optimal ultrasonographic image of the measurement boarder plane 120f of the sample 120 to estimate the defective or the like inside the sample 120.

Figure 8:
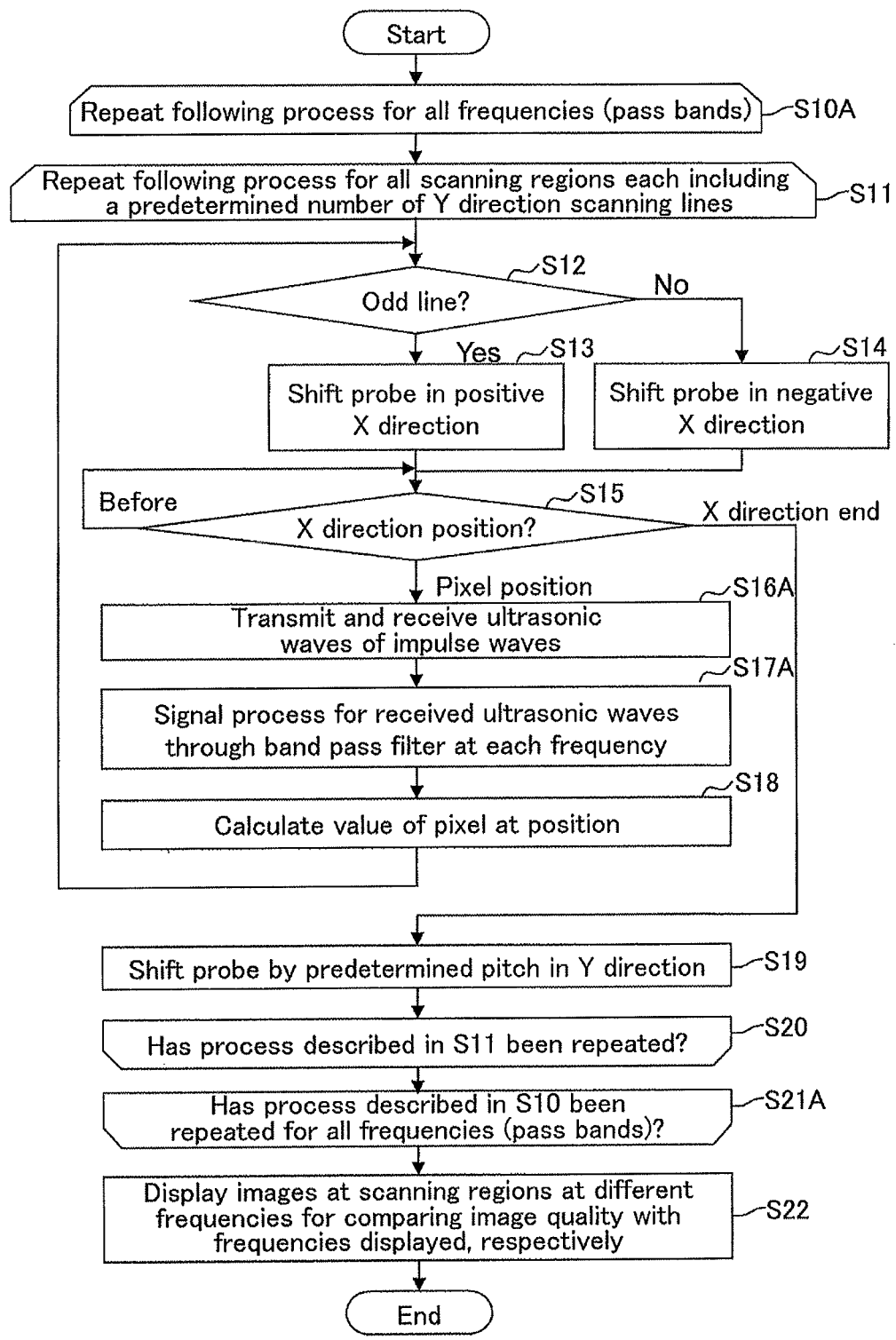
FIG. 8 is a flowchart of generating a frequency-varied image according to a second embodiment.

FIG. 8 is flowchart of a generating process for a frequency-varied image according to a second embodiment.

After a start of the generation process of the frequency-varied image 130, the process from the step S10 to the step S15 are the same as that from the step S10 to the step S15 shown in FIG. 5.

In a step S16A, the timing controller 53 of the image display device 50 effects controlling of transmitting and receiving the ultrasonic waves. In other words, the timing controller 53 controls the impulse wave oscillator 62 to generate and transmit the impulse signal to the piezoelectric device 30. Accordingly, the piezoelectric device 30 transmits the ultrasonic waves having a broad frequency band and receives the echo waves resulting from the ultrasonic waves to convert the echo signal into the received signal. The received signal is amplified by the amplifier 64 and converted with the A/D converter 65 into the digital signal which is inputted into the band-pass filter 67.

In a step S17A, the band-pass filter 67 of the transceiving equipment 60 performs a band pass filter process with a pass-band at the frequency for the received signal on the basis of the output signal of the frequency controller 52A. The signal processing unit 66 performs a signal process for the received signal processed by the band-pass filter 67 on the basis of the gate pulse Vgate. According to this, the image display device 50 can control the frequency of the received signal.

The process from the step S18 to the step S22 are similar to the process from the step S18 to the step S22 of the first embodiment (see FIG. 1).

(Advantageous Effect of Second Embodiment)

As described above the second embodiment provides a following advantageous effect (D).

(D) Because the pass band of the received signal is controlled with the band-pass filter 67, the frequency-varied images 130 can be obtained without any new hardware such as the burst wave oscillator 61.

(Structure of Third Embodiment)

Figure 9:
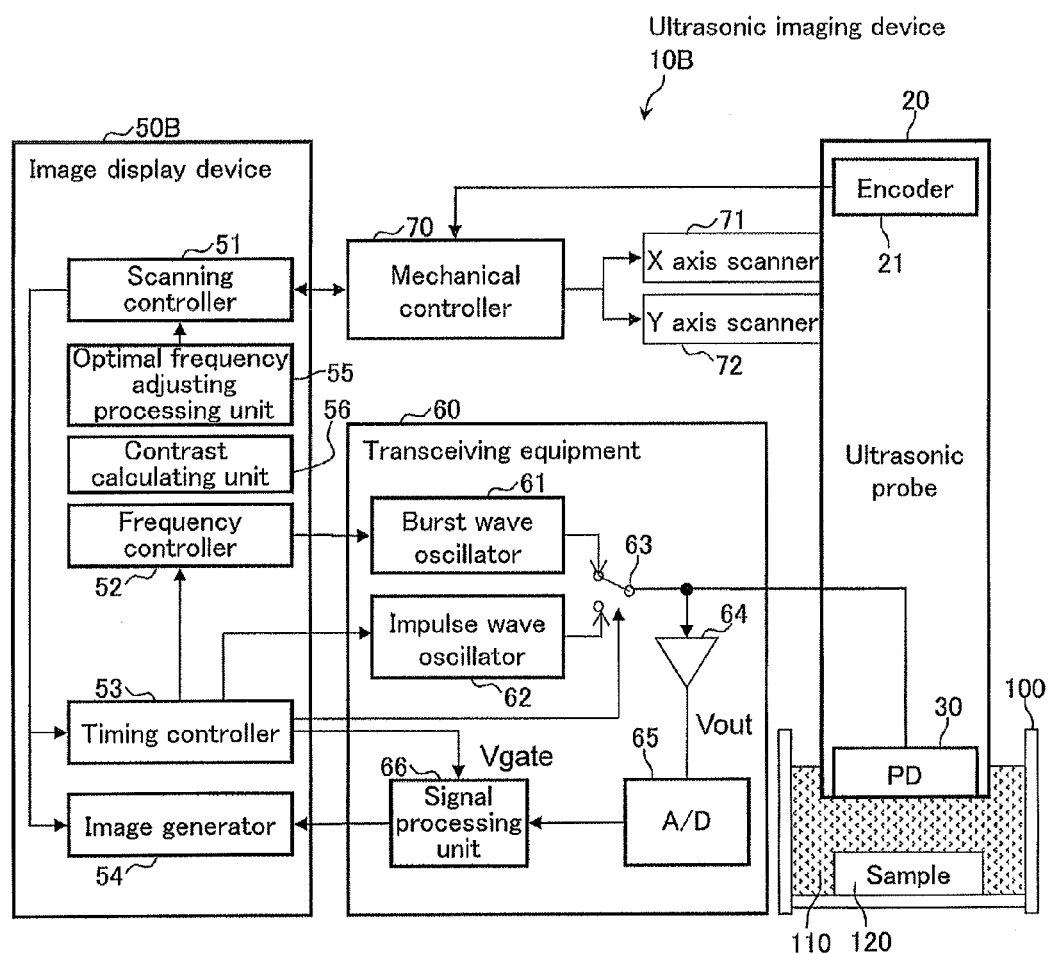
FIG. 9 is a block diagram of the ultrasonic imaging device according to a third embodiment.

FIG. 9 is an outline structure of an ultrasonic imaging device according to a third embodiment.

An ultrasonic imaging device 10B determines a frequency fo of the optimal ultrasonic waves automatically, and obtained the ultrasonographic image at the frequency fo.

The ultrasonic imaging device 10B according to the third embodiment includes an ultrasonic imaging device 50B which is different from the ultrasonic imaging device 10 (see FIG. 1), and other configuration is the same as that of the first embodiment.

The ultrasonic imaging device 50B according to the third embodiment includes in addition to the image display device 50 according to the first embodiment (see FIG. 1), a contrast calculating unit 56 for calculating a contrast of the ultrasonographic image and an optimal frequency adjusting processing unit 55, and other configuration is made similarly to the first embodiment.

The optimal frequency adjusting processing unit 55 controls the scanning controller 51, etc. to estimate the ultrasonographic image of the sample 120, automatically detecting an optimal frequency fo of the ultrasonic waves, to obtain the ultrasonographic image at the detected frequency fo.

The contrast calculating unit 56 calculates the contrast value of the obtained ultrasonographic image. The contrast value is a value obtained by dividing a maximum white brightness value by a black brightness value. The optimal frequency adjusting processing unit 55 determines that the image having the highest contrast value out of the ultrasonographic images is an optimal image and automatically detects the frequency fo of the ultrasonic waves in that case.

(Operation of the Third Embodiment)

An operation of the ultrasonic imaging device according to the third embodiment will be described, occasionally referring to FIG. 7.

In performing the ultrasound test for the sample 120, the operator places the sample 120 on the bottom of the water tank 100.

The operator obtains the ultrasonographic image using the impulse signal to make the measurement boarder plane 120f clear as a target for the sample 120 like the first embodiment.

The operator confirms an echo interval of the measurement boarder plane 120f with reference to the ultrasonographic image of the sample 120 using the impulse signal like the first embodiment and sets timing for turning on the gate pulse Vgate to set the number n of the wave of the burst signal and the frequency f1 to f6. There is a tendency that a resolution in the Z direction decreases when the number n of the waves of the burst signal is too many and that frequency components of the ultrasonic waves includes frequency components other than a desired frequency components when the number of the waves n is too small. The higher the frequency fx of the burst signal becomes, the more the resolution of the image is improved by making the focus of the ultrasonic waves smaller. However, this may result in deterioration in a signal to noise ratio of the image due to attenuation in the water 110 and the inside of the sample 120.

Figure 10:
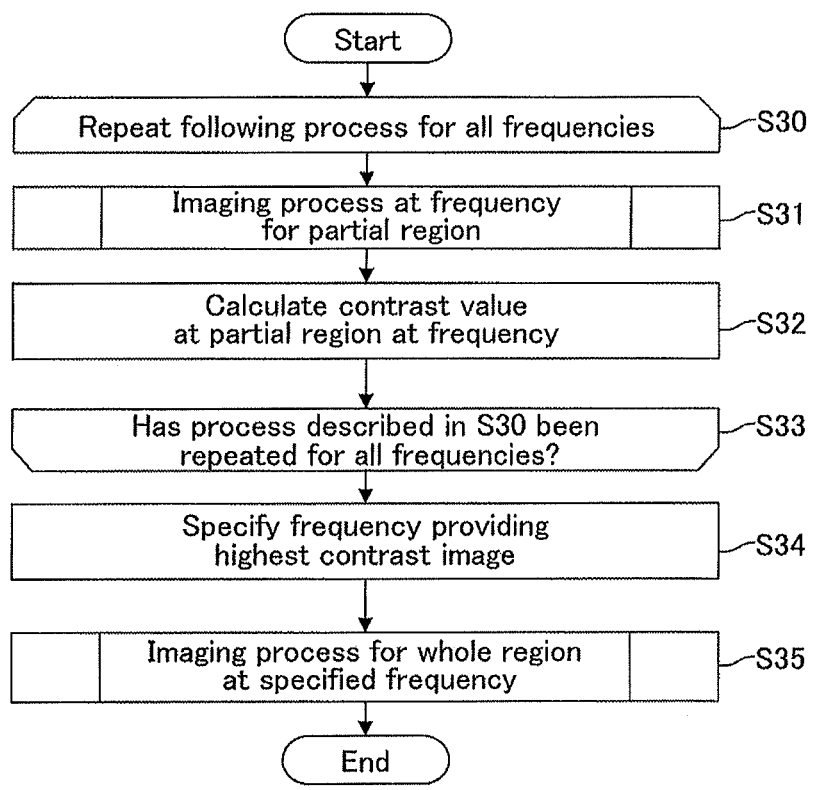
FIG. 10 is a flowchart of an optimal frequency adjusting process according to the third embodiment.

Further the operator switches the signal for the ultrasonic probe 20 from the impulse signal to the burst signal and performs an optimal frequency adjusting process shown in FIG. 10 to obtain an ultrasonographic image of the measurement boarder plane 120f of the sample 120 to estimate a defective inside the sample 120, etc.

FIG. 10 is an optimal frequency adjusting process according to a third embodiment.

When the optimal frequency adjusting process is started, an optimal frequency adjusting processing unit 55 repeats the following steps S30 to S33 for all frequencies. Here, the term "all frequencies" means all frequencies in an adjusting range in the process.

In a step S31, the ultrasonic imaging device 10B performs the imaging process for a partial region at the frequency. Accordingly, the ultrasonic imaging device 10B can generate the ultrasonographic image at the frequency. The partial region is, for example, a region having one fourth of a width of image and one fourth of height at a middle part of the image. Because the ultrasonic imaging device 10B images only a partial region to detect the optimal frequency fo, the optimal frequency fo can be obtain within a short period.

In a step S32, the contrast calculating unit 56 of the ultrasonic imaging device 10B calculates a contrast value of the ultrasonographic image at the frequency.

In a step S33, the optimal frequency adjusting processing unit 55 of the ultrasonic imaging device 10B determines whether the process has been performed for all frequencies. When the determination condition is not established, the optimal frequency adjusting processing unit 55 returns to processing in a step S30.

In a step S34, the optimal frequency adjusting processing unit 55 of the ultrasonic imaging device 10B specifies the frequency providing an image with a highest contrast value. The optimal frequency adjusting processing unit 55 estimates the contrast values of the respective ultrasonographic images with the contrast calculating unit 56 to optimize the frequency of the ultrasonic waves to maximize the contrast value.

In a step S35, the optimal frequency adjusting processing unit 55 of the ultrasonic imaging device 10B performs the imaging process (FIG. 11) for a whole region at the specified frequency and finishes the process in FIG. 10.

Figure 11:
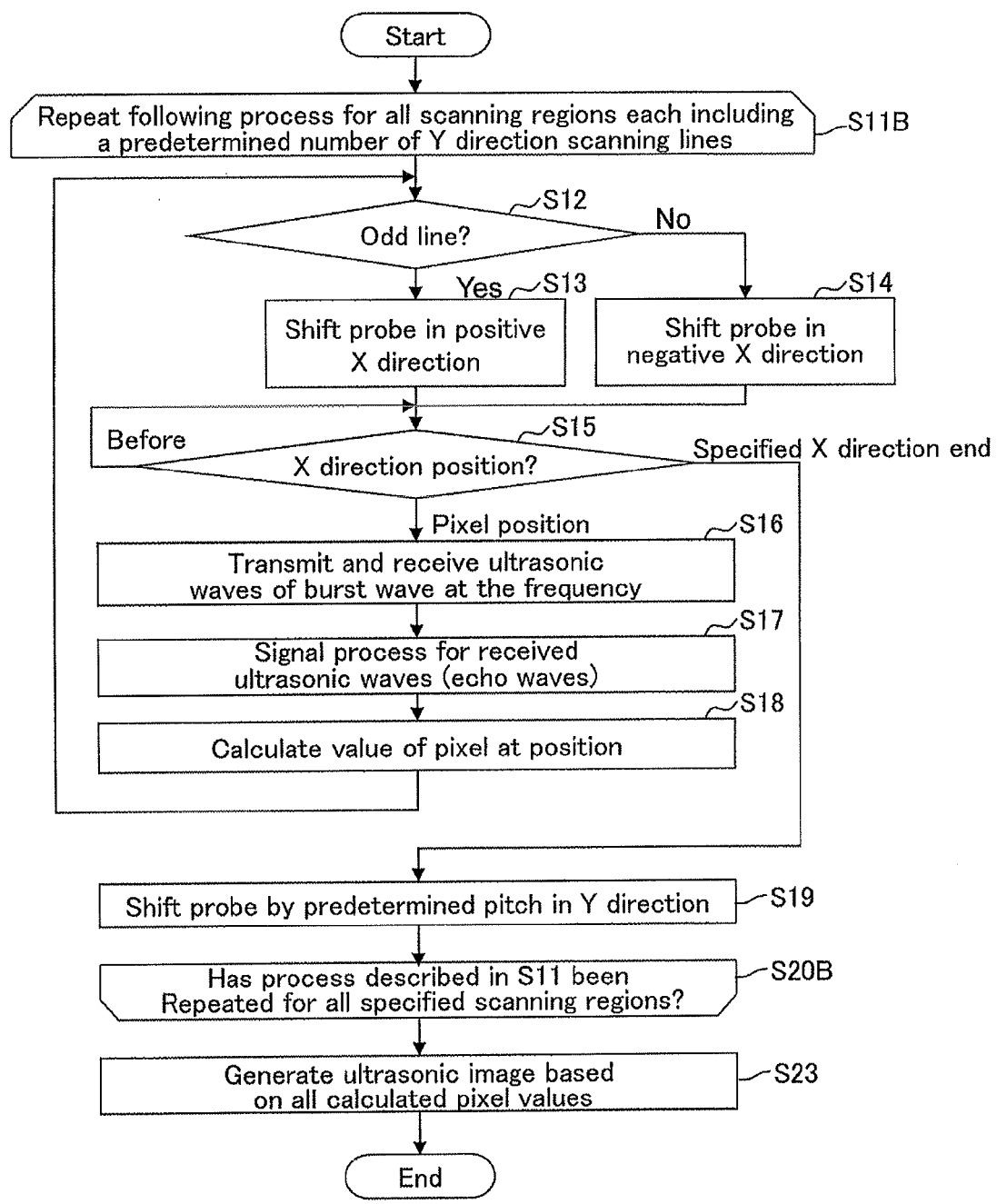
FIG. 11 is a flowchart showing an imaging process according the third embodiment.

FIG. 11 shows an imaging process according to the third embodiment.

The imaging process according to the third embodiment is a process called by the optimal frequency adjusting processing unit 55 of the ultrasonic imaging device 10B in the step S31 and the step S35. In the step S31, the optimal frequency adjusting processing unit 55 performs the imaging process, specifying a partial region of the whole image as a target of imaging to conduct the imaging process. In the step S35, the optimal frequency adjusting processing unit 55 specifies the whole of image as the imaging target to conduct the imaging process.

When the imaging process is started, in a step S11B to a step S20B, the ultrasonic imaging device 10B repeats the process for the specified range including Y direction lines. The term "specified region" means a range specified in the upper level process (step S31 and step S35).

The process of the steps S12 to S19 is the same as the process according to the steps S12 to S19 in the first embodiment.

In the step S20B, the ultrasonic imaging device 10B determines whether the process is repeated for the specified scanning region including a predetermined number of the scanning line in the Y direction. When the determination condition is not established, the ultrasonic imaging device 10B returns to the process in the step S11B.

In a step S23, the image generator 54 of the ultrasonic imaging device 10B generates the ultrasonographic image on the basis of the calculated all pixels, and finishes the process in FIG. 11. Here, "all pixels" means all pixels specified by the upper level process of the imaging process.

(Advantageous Effects of Third Embodiment)

As described above, there are following advantageous effects in the third embodiment.

(E) The ultrasonic imaging device 10B automatically determines whether the image is an optimal inspection image on the basis of the contrast value of the ultrasonographic image. According to this, operator's man power can be saved for the process and the determination.

(F) The optimal frequency of the ultrasonic waves can be determined automatically with a quantitative index not depended on a skillfulness of the operator.

(Modifications)

The present invention is not limited to the embodiments above, but may be modified within a range without departure from sprit of the present invention. There are following modifications (a) to (g).

(a) The embodiments above are examples in which the present invention is applied to the ultrasonic imaging device 10, the ultrasonic imaging device 10A, and the ultrasonic imaging device 10B including the single focus type ultrasonic probe (the ultrasonic probe 20). However, the present invention is not limited to this. The present invention can be applied to the ultrasonic imaging device with an array type ultrasonic probe (the ultrasonic probe 20).

(b) In the embodiments above, the ultrasonic probe 20 transmits the ultrasonic waves, and receives the echo waves reflected by the sample 120 to convert the received echo waves into the received signal. However, the present invention is not limited to this, but may be modified in which an ultrasonic prove for transmission and an ultrasonic prove for reception are provided and the sample is placed on a center area in front of the probes. According to this, the ultrasonic waves reflected, scattered, and refracted by the sample are received and converted into the received signal to generate the ultrasonographic image.

Figure 12:
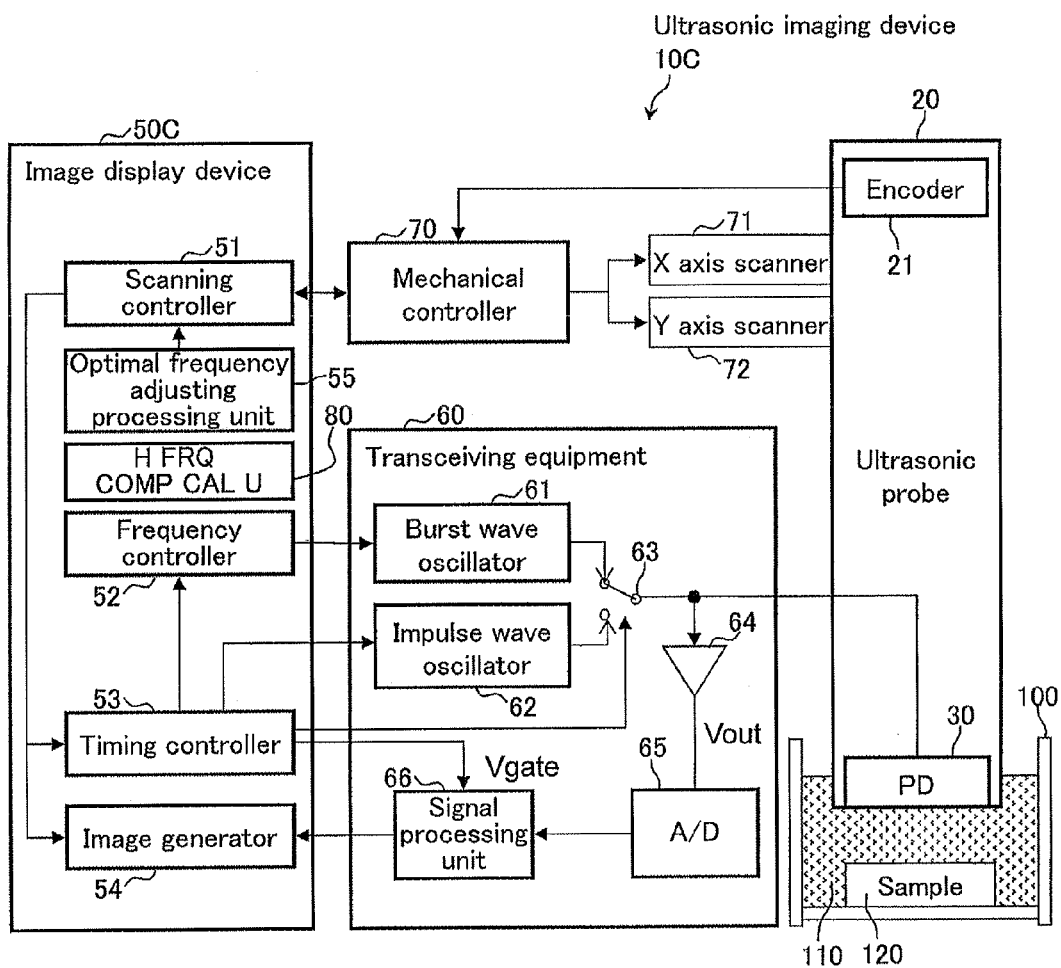
FIG. 12 is a block diagram of a modification of an ultrasonic imaging device which includes a high frequency component calculating unit.

(c) In the third embodiment, the optimal image is determined on the basis of the contrast value. However, this is not limited to this, the ultrasonic imaging device 10 may include a high frequency component estimating unit for estimating the high frequency component of the image, and the frequency of the ultrasonic waves may be optimized to maximize the high frequency component. FIG. 12 shows such a modification of an ultrasonic imaging device 10C which includes an image display device 50C which includes a high frequency component calculating unit 80 for calculating the high frequency component of the image. The optimal frequency adjusting processing unit 55 adjusts the optimal frequency on the basis of the calculated high frequency component of the image.

(d) The sample 120 which a target of the ultrasonic imaging device 10 in the embodiment above is, for example, a semiconductor device or an integrated circuit device. However, the present invention is not limited to this, but may be applied to the general ultrasonic imaging device for non-destructive testing or an ultrasonic imaging device for medical use.

(e) The frequency-varied images 130 in the embodiments above is an ultrasonographic image obtained by varying the frequency stepwise. However, the present invention is not limited to this. For example, the frequency-varied image may be an ultrasonographic image obtained by continuously varying the frequency.

(f) The frequency-varied image 130 in the embodiments above displayed with frequencies displayed on the right hand with marks. However, the present invention is not limited to this. For example, the frequencies may be displayed with values for the frequency-varied image.

(g) The method of varying the frequency is not limited to the embodiments above. For example, the number of pulses is fixed, the frequency is varied for each pulse. Combinations of the number of pulses and the frequencies are registered, and one is successively selected from the combinations. According to this, a variation method for an optimal frequency suited for the material or structure of the sample can be selected and optimal combination between the pulse and the frequency can be selected.

The invention claimed is:

1. A measurement frequency variable ultrasonic imaging device comprising:
   an ultrasonic probe including a piezoelectric device transmitting ultrasonic waves to a sample and receiving ultrasonic waves reflected, scattered, and refracted by the sample to output a received signal;
   a scanner scanning the sample with the ultrasonic probe and positioning the ultrasonic probe at a predetermined scanning position in a Y direction after scanning in an X direction by one line;
   a frequency controller controlling a frequency of the received signal at a predetermined frequency in accordance with the scanning position in the Y direction of the probe, the predetermined frequency being varied stepwise;
   a signal processing unit processing the received signal; and
   an image generator generating an ultrasonic wave image with the predetermined frequency varied stepwise in accordance with the scanning position in the Y direction on the basis of an output signal of the signal processing unit.

2. The measurement frequency variable ultrasonic imaging device as claimed in claim 1, wherein the frequency controller controls the frequency of the received signal by varying a frequency of a transmission signal supplied to the piezoelectric device.

3. The measurement frequency variable ultrasonic imaging device as claimed in claim 1,
   wherein the frequency controller comprises a burst wave oscillator generating and supplying a burst signal having the predetermined frequency to the piezoelectric device.

4. The measurement frequency variable ultrasonic imaging device as claimed in claim 1, wherein the frequency controller controls the frequency of the received signal by controlling a pass band of the received signal.

5. The measurement frequency variable ultrasonic imaging device as claimed in claim 2,
   wherein the frequency controller controls the predetermined frequency of the ultrasonic waves in accordance with the scanning position, and
   wherein the image generator displays the predetermined frequency in accordance with the scanning position on the generated ultrasonic wave image.

6. The measurement frequency variable ultrasonic imaging device as claimed in claim 1, further comprising an optimal frequency adjusting processing unit estimating the ultrasonic wave image of the sample and optimizing the frequency of the ultrasonic waves.

7. The measurement frequency variable ultrasonic imaging device as claimed in claim 6,
wherein the optimal frequency adjusting processing unit comprises a contrast calculating unit and optimizes the frequency of the ultrasonic waves to maximize the contrast.

8. The measurement frequency variable ultrasonic imaging device as claimed in claim 6,
wherein the optimal frequency adjusting processing unit comprises a high frequency component calculating unit calculating a high frequency component of the ultrasonic wave image of the sample and optimizes the frequency of the ultrasonic waves to maximize the high frequency component.

9. The measurement frequency variable ultrasonic imaging device as claimed in claim 1, further comprising:
a burst wave oscillator generating a burst wave having the predetermined frequency;
an impulse wave oscillator generating an impulse wave; and
a switch supplying either of the burst wave or the impulse wave to the piezoelectric device.

10. A measurement frequency variable ultrasonic imaging device comprising:
an ultrasonic probe including a piezoelectric device transmitting ultrasonic waves to a sample and receiving ultrasonic waves reflected, scattered, and refracted by the sample to output a received signal;
a scanner scanning the sample with the ultrasonic probe and positioning the ultrasonic probe at a predetermined scanning position in a Y direction after scanning in an X direction by one line;
a frequency controller varying a frequency of the transmitting ultrasonic waves of the piezoelectric device at a predetermined frequency stepwise in accordance with the scanning position in the Y direction of the probe;
a signal processing unit processing the received signal; and
an image generator generating one sheet of an ultrasonic wave image with the predetermined frequency varied stepwise in accordance with the scanning position in the Y direction on the basis of an output signal of the signal processing unit.

* * * * *